United States Patent [19]

Re

[11] Patent Number: 4,514,173

[45] Date of Patent: Apr. 30, 1985

[54] DENTURE COUPLING

[76] Inventor: Eugene L. Re, 1920 SW. 52nd Ter., Plantation, Fla. 33317

[21] Appl. No.: 229,827

[22] Filed: Jan. 30, 1981

[51] Int. Cl.$^3$ ............................................. A61C 13/02
[52] U.S. Cl. ................................................... 433/178
[58] Field of Search ............... 433/178, 172, 177, 192, 433/193, 194

[56] References Cited

U.S. PATENT DOCUMENTS

| | | | |
|---|---|---|---|
| 703,720 | 7/1902 | Dunn. | |
| 1,425,844 | 8/1922 | Engberg | 433/178 |
| 1,426,935 | 8/1922 | Wiechert | 433/178 |
| 2,682,706 | 7/1954 | Johnson | 32/5 |
| 3,047,952 | 8/1962 | Yamamoto | 32/5 |
| 3,716,918 | 2/1973 | Tole et al. | 32/5 |

*Primary Examiner*—Robert Peshock
*Attorney, Agent, or Firm*—Fuller, House & Hohenfeldt

[57] ABSTRACT

A prosthetic denture which releasably engages natural abutment teeth to releasably hold it in place in the user's mouth. The denture has a continuous lingual flange and a buccal flange which is interrupted adjacent at least one tooth of a consecutive series of remaining natural teeth. The denture is held in place by gasketed horseshoe-shaped clasping and sealing members extending anteriorly of the remaining portions of the buccal flange. The clasping and sealing members can be integral extensions of the denture base material. The denture is particularly adapted for users having a series of consecutive natural teeth, particularly if the user's gum adjacent those natural teeth is substantially undercut.

1 Claim, 5 Drawing Figures

DENTURE COUPLING

TECHNICAL FIELD

The invention relates to prosthetic upper or lower denture appliances which utilize one or more remaining natural teeth in the user's mouth to locate and assist in securing the denture.

BACKGROUND ART

The denture art has long known of clasping devices, usually a metal clasp with protruding ends which embrace an abutment tooth, to secure a denture in place. These conventional clasping devices are incapable of forming a seal with the abutment teeth they embrace. As a result, food can become lodged between the clasp and the tooth, causing decay and other problems. As well, metal clasps are likely to damage the abutment teeth and the tissue of a user's mouth, causing injury and pain.

More recently, dentures have been formed with gasketed apertures through which the anchoring teeth pass when the denture is inserted in the user's mouth. Such dentures and methods of making the same are described in U.S. Pat. No. 3,716,918, issued to Tole, et al. on Feb. 20, 1973. That patent is hereby incorporated by reference in the present specification. Although the denture of the Tole patent represents a significant advance over the preexisting art, there is still room for improvement in the device of the Tole patent. The device of that patent is usually difficult or impossible to insert in the user's mouth when the user's five and six anterior teeth are intact, and especially if the user's bicuspids are also intact. When numerous natural teeth remain in the user's mouth, the deviations of the surfaces of natural teeth and gums from an orientation parallel to the path of insertion can prevent the appliance from being seated successfully if it includes a closed labial flange.

The device of Tole can also be significantly improved when the user's gums are substantially undercut, meaning that a gap remains between the buccal flange of the denture and the buccal surface of the corresponding natural gum when the denture is in place. Food can lodge in this gap. Also, air can enter between the denture and the user's mouth surfaces through this gap, destroying the suction which aids in securing the denture in place. It will be evident that the denture cannot be adapted to fill this undercut by building up the inner surface of the buccal flange of the denture, for that expedient would make the denture impossible to insert in the user's mouth.

SUMMARY OF THE INVENTION

The present invention is an improved denture of the type adapted for repetitive detachable engagement with at least the terminal teeth of a series of consecutive remaining natural teeth, said denture comprising buccal and lingual flanges depending from an artifical tooth anchoring portion. The buccal flange has first and second separated portions extending generally posteriorly of the abutment teeth so that the denture has no buccal flange adjacent at least one of the consecutive remaining natural teeth. Horseshoe-shaped clasping and sealing members extend forward from the first and second separated portions of the buccal flange. These clasping and sealing members releasably engage the natural surfaces of at least said terminal teeth for securing and positioning the denture, and for forming a seal to prevent air from entering under the denture. Suction can then assist in maintaining the denture in position.

Surprisingly, even though the horseshoe-shaped clasping and sealing members do not encircle the abutment tooth or teeth and the buccal flange is not continuous, the denture still seats against the user's teeth and gums sufficiently to allow the seal between the denture and the user's mouth to be maintained.

DETAILED DESCRIPTION OF THE PREFERRED EMBODIMENT

Although the disclosure hereof is detailed and exact to enable those skilled in the art to practice the inventon, the physical embodiments herein disclosed merely exemplify the invention which may be embodied in other specific structure. While the best known embodiment has been described, the details may be changed without departing from the invention, which is defined by the claims.

Figure 1:
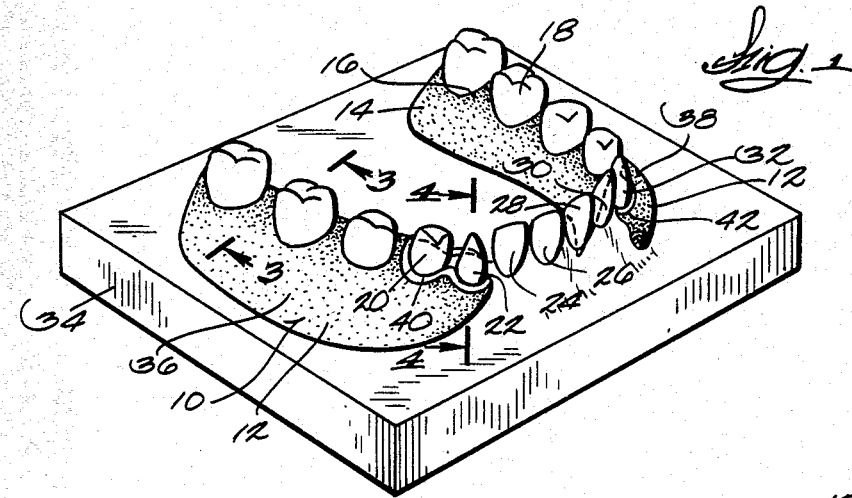
FIG. 1 is a perspective view of a denture according to the present invention seated on a dental stone counterpart of the user's remaining natural teeth and gum.

In the drawing, FIG. 1 shows a denture 10 formed in the conventional manner from acrylic or plastic material. The denture 10 has a buccal flange 12 and a lingual flange 14 which duplicate as nearly as possible the user's gums. Flanges 12 and 14 depend from an artificial tooth anchoring portion 16 to which are secured the several artifical teeth such as 18 which correspond to natural teeth the user lacks. In the embodiment of FIG. 1, the wearer still has a series of consecutive remaining natural teeth—20, 22, 24, 26, 28, 30, and 32. Of these teeth, teeth 20 and 32 are the terminal teeth of a consecutive series. These teeth are reproduced in the dental stone counterpart 34, which also reproduces the wearer's natural gum.

Buccal flange 12 has first and second separated portions 36 and 38 which extend generally posteriorly of terminal teeth 20 and 32. The lingual flange of the denture, in contrast to the buccal flange, is substantially continuous along the entire dental arch.

The denture is secured to the abutment teeth by horseshoe-shapd clasping and sealing members 40 and 42. (As used herein, the term "horseshoe-shaped" denotes an open ended clasp which is so shaped as to embrace at least one tooth.) Each clasping and sealing member is an integral extension of the rigid denture material having inner walls which closely conform to the contours of the embraced teeth. Each clasping and sealing member is lined with an elastomeric partial gasket such as 44 which can be formed substantially as taught in the Tole patent referenced above. The gasket 44 seats intimately against the neck portion of at least the terminal tooth of a consecutive series of at least three teeth.

Figure 2:
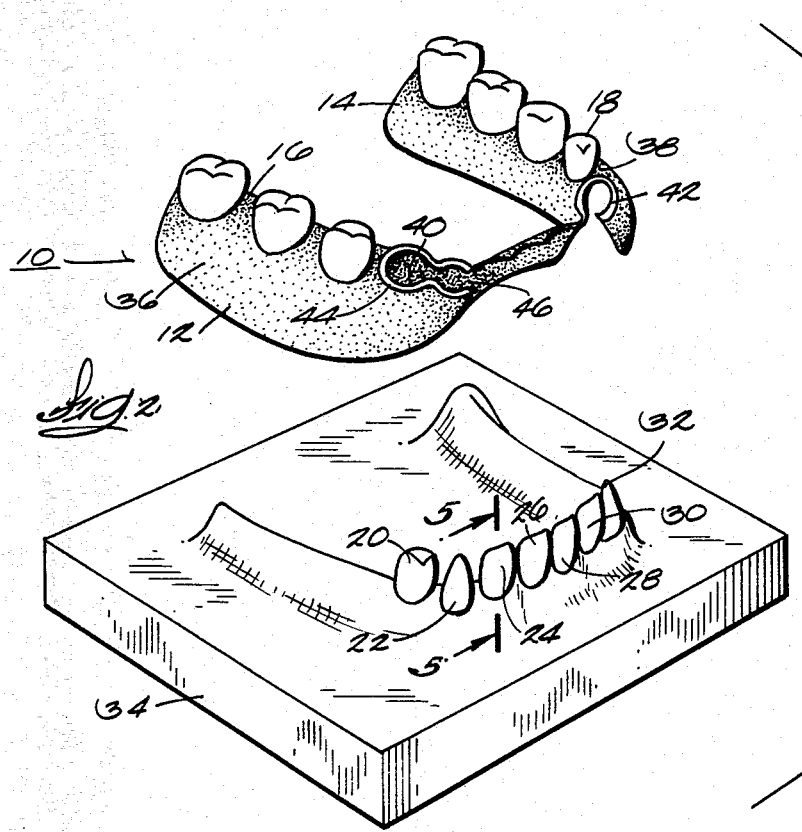
FIG. 2 is similar to FIG. 1, but shows the denture and counterpart separated.

The open end 46 of partial gasket 44 is provided in order to allow the denture to be seated in the user's mouth or on the dental stone counterpart even though the wearer has a series of consecutive remaining teeth. FIG. 2 illustrates that the clasping and sealing member can embrace a single tooth, as does clasping sealing member 42, or it may embrace two or more teeth, as does clasping and sealing member 40. But at least some of the centrally located teeth in the consecutive series, (here, teeth 24, 26 and 28) are not embraced by clasping and sealing members.

Figure 3:
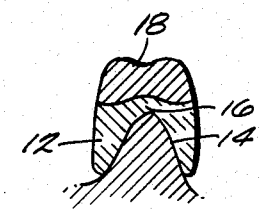
FIG. 3 is a cross section taken along line 3—3 of FIG. 1.
Figure 4:
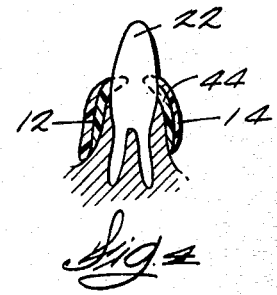
FIG. 4 is a cross section taken along line 4—4 of FIG. 1.

FIGS. 3 and 4 show the structure of the denture and counterpart of FIG. 1 in more detail.

Figure 5:
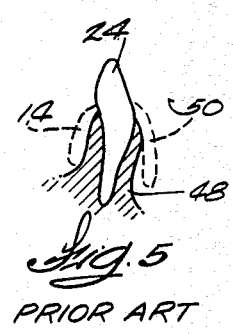
FIG. 5 is a cross section taken along line 5—5 of FIG. 2, with a section through a prior art denture added in broken lines to show its position when seated in the user's mouth.

The reason for providing an interrupted buccal flange in the denture is shown in FIG. 5, in which a denture according to the prior art is superimposed on a cross section of an anterior portion of the arch of the stone counterpart. As is frequently the case, the user's outer gum adjacent tooth 24 of FIG. 5 has an undercut region 48 which allows foreign matter to accumulate between buccal flange 50 and the user's gum. This undercut region also allows air to infiltrate between the positioned denture and the base on which it rests in the user's mouth. Accumulations of material in the undercut region 48 can also cause the denture to be improperly seated. At the same time the prior art buccal flange portion 50 in front of the user's gum as shown in FIG. 5 is sometimes visible when the patient opens his or her mouth, thus causing embarrassment.

It has been surprisingly found that the denture shown in FIGS. 1 through 4 provides a superior fit and thus allows the denture to form a substantially airtight seal in the user's mouth, despite the omitted portions of the buccal flange and the use of horseshoe-shaped elastomeric gaskets. The present invention thus provides a denture which seats more readily in the user's mouth, which seals substantially as well as the prior art denture, and yet which omits the bulky and otherwise objectionable anterior portion of the buccal flange.

I claim:

1. In a prosthetic denture of the type adapted for repetitive detachable engagement with at least the terminal teeth of a series of consecutive remaining natural teeth, said denture comprising buccal and lingual flanges depending from an artificial tooth anchoring portion thereof, said buccal flange having first and second separated portions extending generally posteriorly of said terminal teeth, wherein a portion of said denture positioned adjacent at least one of said remaining natural teeth has no buccal flange; the improvements comprising:

A. clasping members defined by horseshoe-shaped walls integrally formed in the anterior ends of said first and second separated portions to embrace the neck portions of at least said terminal teeth; and B. a sealing member for each wall comprising elastomeric material bonded to and substantially coextensive with said wall for forming a continuous line seal between said wall and the embraced portion of the terminal teeth;

whereby to anchor said denture to said terminal teeth while preventing the entry of foreign matter between said walls and the embraced portions of said teeth.

* * * * *